United States Patent [19]

Stumpf

[11] 3,994,288
[45] Nov. 30, 1976

[54] COLPOSCOPE
[75] Inventor: Joseph G. Stumpf, Fairfield, Conn.
[73] Assignee: Frigitronics of Conn., Inc., Shelton, Conn.
[22] Filed: June 11, 1975
[21] Appl. No.: 585,781

[52] U.S. Cl. .................................. 128/6; 350/19; 354/79; 351/7; 128/8
[51] Int. Cl.² ........................ A61B 1/22; A61B 1/04
[58] Field of Search ................ 128/5, 6, 7, 8, 9, 10, 128/11; 350/19, 33, 18; 354/79, 62, 63; 351/7

[56] References Cited
UNITED STATES PATENTS

| | | | |
|---|---|---|---|
| 2,482,971 | 9/1949 | Golson | 128/6 |
| 2,691,918 | 10/1954 | Robins et al. | 350/19 |
| 2,737,079 | 3/1956 | Brown et al. | 350/18 |
| 3,089,398 | 5/1963 | Wilms | 354/62 X |
| 3,545,355 | 12/1970 | Cahall, Jr. | 350/19 |
| 3,638,643 | 2/1972 | Hotchkiss | 128/9 |
| 3,798,665 | 3/1974 | Eloranta | 350/19 |

Primary Examiner—Aldrich F. Medbery
Attorney, Agent, or Firm—Buckles and Bramblett

[57] ABSTRACT

A colposcope including a camera selectively mountable to take photographs along one optical axis of the binocular microscope and a flash unit for illuminating the field of examination along the optical axis of the colposcope illuminator by means of a mirror selectively postionable in the optical axis of the illuminator.

The foregoing abstract is not to be taken either as a complete exposition or as a limitation of the present invention. In order to understand the full nature and extent of the technical disclosure of this application, reference must be had to the following detailed description and the accompanying drawings as well as to the claims.

16 Claims, 4 Drawing Figures

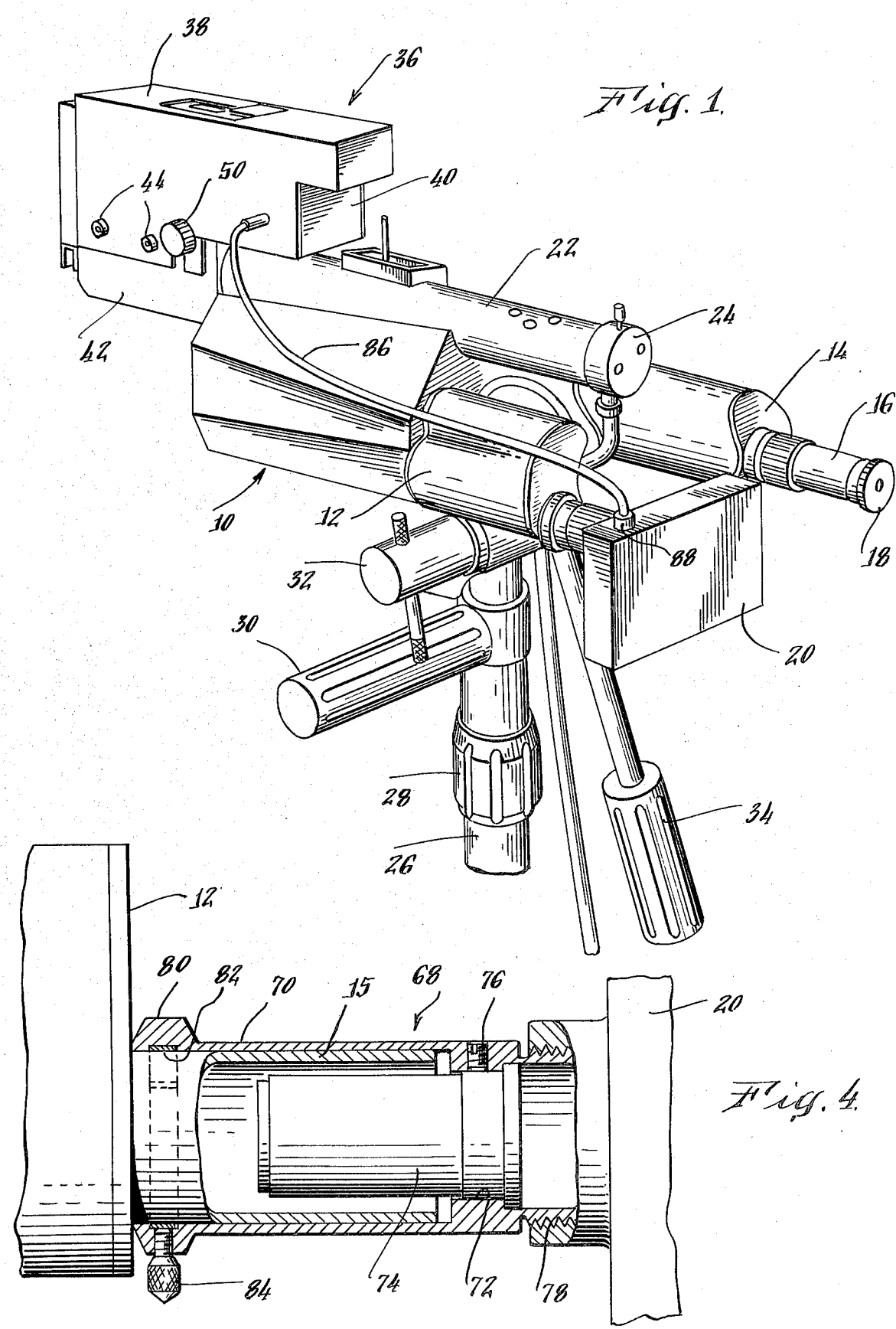

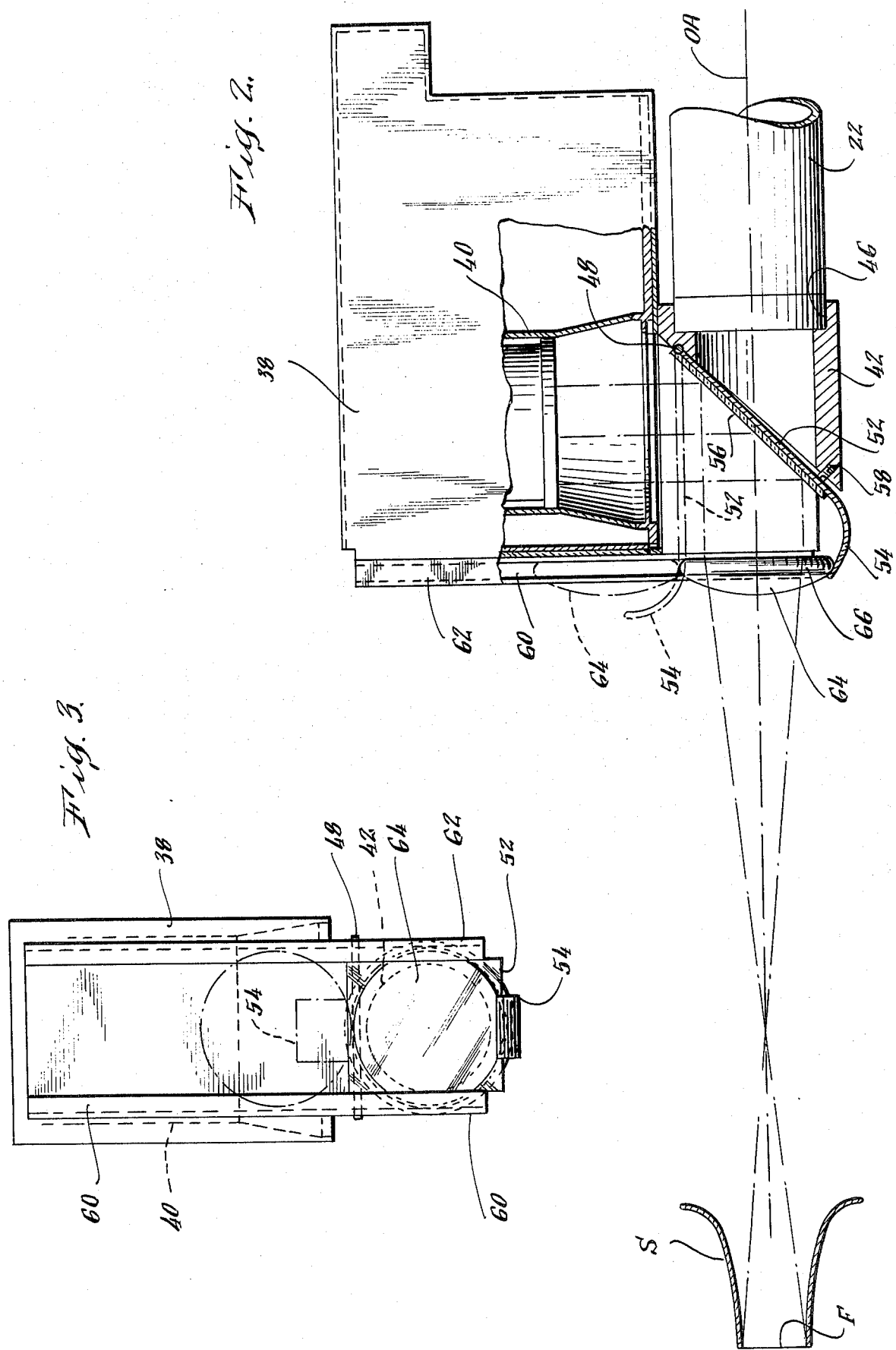

COLPOSCOPE

BACKGROUND OF THE INVENTION

Colposcopes are routinely employed by physicians to examine the vaginal area through a speculum. These instruments comprise a binocular microscope and an illuminating unit. As a result of the restricted field of view, it is necessary to keep the axes of the binocular microscope and the axis of the illumination means in close physical proximity. Physicians often desire to photograph the field of examination to thereby obtain a permanent record. Accordingly, special colposcopes are available but, unfortunately, these are usually too expensive for the average physician's office and are usually available only in clinics and hospitals. The reason for the additional expense is that separate optical systems are required for the camera and for the flash unit. This means that a total of five optical axes must converge upon the same field of view. The close tolerances and additional complexity thus introduced substantially increase the cost of such colposcopes.

Accordingly, it is a primary object of the present invention to provide a photographing colposcope of reduced cost, easily affordable by a physician for office use. Another object is to provide such a colposcope which does not require separate optical systems for either the camera or the flash unit. Another object is to provide such a colposcope which employs the optical systems of the microscope and the microscope illuminator for photographing purposes. Other objects, features, and advantages will become apparent from the following description and appended claims.

SUMMARY OF THE INVENTION

The objects of this invention are achieved by an improvement in a medical examining instrument of the type including a binocular microscope having first and second ocular assemblies and an illuminating unit, the optical axis of the illuminating unit being closely adjacent the optical axes of the microscope. The improvement comprises a photographic flash unit which is positioned to direct radiation into the path of illumination from the illuminating unit at an angle to its optical axis. Means are provided which are selectively positionable in the illumination path for redirecting radiation from the flash unit along the optical axis of the illuminating unit. Camera means are selectively mountable on one of the ocular assemblies to photograph the field of view of the microscope.

BRIEF DESCRIPTION OF THE DRAWINGS

FIG. 1 is a perspective view of a colposcope in accordance with the present invention;

FIG. 2 is an elevational view of the photographic flash unit of the present invention, partially broken away to illustrate its internal construction;

FIG. 3 is a left end view of the flash unit of FIG. 2, illustrating its operation; and FIG. 4 is a top view, in partial cross section, illustrating the mounting of the camera to the microscope.

DESCRIPTION OF THE PREFERRED EMBODIMENT

With particular reference to FIG. 1, there is illustrated a colposcope in accordance with this invention which comprises a conventional binocular microscope 10 including left 12 and right 14 ocular assemblies, each having an eye tube 15, 16 which normally carries in its end an eye piece 18. In the illustration of FIG. 1, the left eye piece is removed and replaced by a camera 20 as will be later explained. The camera obscures the left eye tube 15. Mounted atop the microscope 10 is an illumination unit 22, including a lamp assembly 24. The optical axes of the microscope 10 and the optical axis of the illumination unit 22 are closely spaced to permit illumination and observation of a limited field of view within a vaginal speculum. The colposcope is mounted upon the usual stand 26 and includes the usual adjustment devices such as a gross vertical adjustment 28, fine vertical adjustment 30, angular lock 32, and focus and angular adjustment 34.

The description so far presented is that of a conventional colposcope. However, unconventionally mounted at the forward end of illumination unit 22 is a flash assembly 36. The flash assembly 36 comprises a box-like outer housing 38 enclosing a conventional electronic flash unit 40. The bottom of housing 38 is open, and the spaced sides are secured to a substantially semicircular mounting base 42, by means of screws 44. The mounting base 42 is substantially hollow and defines a circular opening 46 which, as shown in FIG. 2., fits over the end of the illumination unit 22.

A shaft 48 extends horizontally across the upper portion of the mounting base 42 and through suitable openings in the sides thereof. An adjusting knob 50 is secured to each end of the shaft 48. Secured to and depending from the shaft 48 is a metal plate 52, curved at its lower end to define a vertical lip 54. Secured to the upper surface of the plate 52 is a flat mirror 56. It will thus be seen, as shown in FIG. 2, that the plate 52 is movable between a raised position shown in dashed-dotted lines, which is removed from the optical axis OA of illumination unit 22 and a lowered position (illustrated) wherein it angularly obstructs the optical axis of the illumination unit at an angle of approximately 45°. This angle is adjustable by means of a stop such as set screw 58. Plate 52 may be held in either a raised or lowered position by friction or suitable means, such as springs.

Carried on the front of the housing 38 are a pair of spaced, vertical channels 60, 62. Slidably mounted between these channels is a condensing lens 64. The edge of the lens 64 is enclosed within a suitable wear resistant material 66, such as a plastic, to prevent damage to the optical surface. As will be seen from FIG. 2., the lens rests against the lip 54 of plate 52 and is vertically slidable between a raised position illustrated in dashed-dotted lines and a lowered position in alignment with optical axis OA of the illumination unit 22.

In accordance with the present invention, the camera 20 is selectively mounted upon one of the two ocular assemblies of the microscope 10, in a manner illustrated most clearly by FIG. 4. The camera 20, which may be either a standard 33 mm camera or a self-processing camera, is modified by removal of the camera lens which is replaced by an adapter assembly 68. The adapter assembly comprises a cylindrical housing 70, which has an internal dimension enabling it to be slipped over the eye tube 15 (or 16) when the corresponding eye piece is removed. The inner surface of the housing 70 defines an annular shoulder 72 which supports an ocular lens assembly 74 retained by means of a set screw 76. The housing 70 is mounted on the camera 20 by means of threads 78, or other suitable connection. The end of the housing 70, which is remote from the camera 20, carries a boss 80 having an internal recess within which is mounted a split ring 82. A clamping screw 84 extends through a tapped hole in the boss 80 and into engagement with the ring 82. By means of this assembly, the ocular lens is displaced sufficiently to compensate for the difference between an observer's retinal distance and the film distance. A cable 86 is connected between the camera flash connector 88 and the electronic flash unit 40.

OPERATION

For normal use as a colposcope, the camera 20 would not be mounted upon the microscope shown in FIG. 1, in order that the microscope might operate binocularly in the usual manner. The flash assembly 36 would be mounted upon the illumination unit 22 as illustrated. However, the plate 52 and its reflecting mirror 56 would be raised to the horizontal position illustrated by the dashed-dotted lines in FIG. 2, thus clearing the optical axis OA of the illumination unit and maintaining the condensing lens 64 in the raised position within the channels 60, 62. The physician would then utilize the colposcope in the usual manner for viewing the field of interest.

If the physician should decide to photograph the field, he would simply remove the eye piece from the eye tube 15 and would replace it with the camera carrying adapter assembly 68. As shown in FIG. 4, the adapter assembly is pushed in place over the eye tube 15 and the set screw 84 is tightened to clamp the split ring 82 thereon. He would connect the cable 86 to the flash unit 36.

As the right ocular would remain unobstructed, the physician could continue to observe the field of view through it and, when ready to take a picture, would rotate the knobs 50 on the flash unit so as to rotate shaft 48 and lower the plate 52 and mirror 56 into the position illustrated in FIG. 2. Upon downward rotation of this plate, the condensing lens 64 supported by the lip 54 would slide downwardly within the channels 60, 62 into position on optical axis OA as illustrated in FIG. 2. As will be seen from this illustration, the light from the flash assembly 40 is directed downwardly against the mirror which redirects it along the same optical axis OA as that of the illumination unit 22 and through the condensing lens 64 which images the electronic flash on the field of view F through the speculum S. Accordingly, once the mirror is lowered into this position, the physician merely actuates the camera shutter, initiating the flash and taking the picture through the same optical axis as that of the microscope.

It will now be apparent that the invention disclosed herein permits the physician to photograph the desired field of view utilizing the existing optical elements of a conventional colposcope without requiring additional optical systems as required by conventional photographing colposcopes. The camera 20 employed by the physician may be of any preferred type. However, it is believed that most physicians will prefer to employ a self-processing type of camera as this permits him to determine immediately whether the photograph is satisfactory. It also permits the photograph to be marked immediately with identifying indicia, thus preventing any possibility of mix-ups as might occur if a roll of film were to be developed at some future date.

It is believed that the many advantages of this invention will now be apparent to those skilled in the art. It will also be apparent that a number of variations and modifications may be made therein without departing from its spirit and scope. Accordingly, the foregoing description is to be construed as illustrative only, rather than limiting. This invention is limited only by the scope of the following claims.

I claim:

1. In a medical examining instrument of the type including a binocular microscope having first and second ocular assemblies and an illuminating unit, the optical axis of said illuminating unit having a path closely adjacent the optical axes of said microscope, the improvement which comprises: a photographic flash unit positioned at an angle to said optical axis path to direct its radiation into the path of illumination from said illuminating unit at an angle to its optical axis; means selectively positionable in said illumination path for obscuring said illumination path and directing radiation from said flash unit along the optical axis of said illuminating unit; and camera means selectively mountable on one of said ocular assemblies to photograph the field of view of said microscope therethrough.

2. The improvement of claim 1 wherein said directing means comprises: a reflector movable between a first position out of the path of radiation from said illuminating unit and a second position blocking said path.

3. The improvement of claim 2 wherein said directing means comprises means for concentrating said flash unit radiation on the field of view of said microscope.

4. The improvement of claim 3 wherein said concentrating means comprises a lens.

5. The improvement of claim 2 wherein said reflector comprises a mirror pivotally mounted for rotation between a raised first position and a lowered second position.

6. The improvement of claim 5 wherein said directing means comprises means for concentrating said flash unit radiation on the field of view of said microscope.

7. The improvement of claim 6 wherein said concentrating means is movable between a first position out of the path of radiation from said illuminating unit and a second position in the path of said flash unit radiation.

8. The improvement of claim 7 wherein said concentrating means is a lens movable between said first and second positions by rotation of said pivoted mirror.

9. In a medical examining instrument of the type including a binocular microscope having first and second ocular assemblies and an illuminating unit, the optical axis of said illuminating unit having a path closely adjacent the optical axes of said microscope, the improvement which comprises: a photographic flash unit positioned at an angle to said optical axis path to direct its radiation into the path of illumination from said illuminating unit at an angle to its optical axis; means selectively positionable in said illumination path for obscuring said illumination path and directing radiation from said flash unit along the optical axis of said illuminating unit; and at least one of said ocular assemblies being adapted to receive a means for recording images.

10. The improvement of claim 9 wherein said directing means comprises: a reflector movable between a first position out of the path of radiation from said illuminating unit and a second position blocking said path.

11. The improvement of claim 10 wherein said directing means comprises means for concentrating said flash unit radiation on the field of view of said microscope.

12. The improvement of claim 11 wherein said concentrating means comprises a lens.

13. The improvement of claim 10 wherein said reflector comprises a mirror pivotally mounted for rotation between a raised first position and a lowered second position.

14. The improvement of claim 13 wherein said directing means comprises means for concentrating said flash unit radiation on the field of view of said microscope.

15. The improvement of claim 14 wherein said concentrating means is movable between a first position out of the path of radiation from said illuminating unit and a second position in the path of said flash unit radiation.

16. The improvement of claim 15 wherein said concentrating means is a lens movable between said first and second positions by rotation of said pivoted mirror.

* * * * *